United States Patent
Chellppannair et al.

(10) Patent No.: US 10,358,394 B2
(45) Date of Patent: Jul. 23, 2019

(54) MTO PROCESS FOR ENHANCED PRODUCTION OF PROPYLENE AND HIGH VALUE PRODUCTS

(71) Applicant: UOP LLC, Des Plaines, IL (US)

(72) Inventors: Thulasidas Chellppannair, Cave Creek, AZ (US); Nicholas J. Schoenfeldt, Chicago, IL (US); Andrea G. Bozzano, Northbrook, IL (US); Wolfgang A. Spieker, Glenview, IL (US); Christopher D. DiGiulio, Chicago, IL (US); Gregory A. Funk, Carol Stream, IL (US); Jaime G. Moscoso, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/617,934

(22) Filed: Jun. 8, 2017

(65) Prior Publication Data
US 2017/0297972 A1  Oct. 19, 2017

Related U.S. Application Data

(63) Continuation of application No. PCT/US2015/063649, filed on Dec. 3, 2015.

(60) Provisional application No. 62/090,674, filed on Dec. 11, 2014.

(51) Int. Cl.
| | |
|---|---|
| *C07C 1/20* | (2006.01) |
| *B01J 29/85* | (2006.01) |
| *C07C 4/06* | (2006.01) |
| *C07C 6/04* | (2006.01) |
| *B01J 38/12* | (2006.01) |
| *B01J 29/90* | (2006.01) |

(52) U.S. Cl.
CPC .............. *C07C 1/20* (2013.01); *B01J 29/85* (2013.01); *C07C 4/06* (2013.01); *C07C 6/04* (2013.01); *B01J 29/90* (2013.01); *B01J 38/12* (2013.01); *C07C 2529/85* (2013.01); *Y02P 20/52* (2015.11); *Y02P 20/584* (2015.11); *Y02P 30/42* (2015.11)

(58) Field of Classification Search
CPC .......... C07C 1/20; C07C 6/04; C07C 2529/85
See application file for complete search history.

(56) References Cited

U.S. PATENT DOCUMENTS

| | | |
|---|---|---|
| 5,914,433 A | 6/1999 | Marker |
| 6,137,022 A | 10/2000 | Kuechler et al. |
| 6,303,839 B1 | 10/2001 | Marker |

(Continued)

FOREIGN PATENT DOCUMENTS

RU  2342357 C2  12/2008

OTHER PUBLICATIONS

Chen et al. ("SAPO-18 Catalysts and Their Bronsted Acid Sites", J. Phys. Chem. 1994, 98, pp. 10216-10224) (Year: 1994).*

(Continued)

*Primary Examiner* — Brian A McCaig
*Assistant Examiner* — Jason Y Chong (57) ABSTRACT

A process is presented for the production of light olefins. The process utilizes a SAPO-18 catalyst and is operated at an elevated pressure. The process generates higher concentrations of heavier olefins which can then be processed to generate light olefins. The processing of the heavier olefins can include metathesis reactions and olefin cracking processes.

9 Claims, 5 Drawing Sheets

(56) References Cited

U.S. PATENT DOCUMENTS

| | | | |
|---|---|---|---|
| 6,506,954 B1* | 1/2003 | Brown | C07C 1/20 |
| | | | 585/469 |
| 6,531,639 B1* | 3/2003 | Fung | C07C 1/20 |
| | | | 585/326 |
| 7,317,133 B2 | 1/2008 | Vora et al. | |
| 7,568,016 B2 | 7/2009 | Gilbert | |
| 7,732,650 B2 | 6/2010 | Bozzano et al. | |
| 7,763,765 B2 | 7/2010 | Kuechler et al. | |
| 2005/0033104 A1* | 2/2005 | van Egmond | C07C 7/11 |
| | | | 585/800 |
| 2008/0081936 A1* | 4/2008 | Bozzano | C07C 1/20 |
| | | | 585/639 |
| 2008/0154078 A1* | 6/2008 | Bozzano | C07C 1/20 |
| | | | 585/317 |
| 2009/0292151 A1 | 11/2009 | Bozzano et al. | |
| 2012/0130137 A1* | 5/2012 | Orita | B01J 23/002 |
| | | | 585/621 |

OTHER PUBLICATIONS

Search Report dated Mar. 10, 2016 for corresponding PCT Appl. No. PCT/US2015/063649.

* cited by examiner

MTO PROCESS FOR ENHANCED PRODUCTION OF PROPYLENE AND HIGH VALUE PRODUCTS

CROSS-REFERENCE TO RELATED APPLICATIONS

This application is a Continuation of copending International Application No. PCT/US2015/063649 filed Dec. 3, 2015, which application claims priority from U.S. Provisional Application No. 62/090,674 filed Dec. 11, 2014, now expired, the contents of which cited applications are hereby incorporated by reference in their entirety.

FIELD OF THE INVENTION

The present invention relates to the conversion of oxygenates to olefins. In particular, this invention relates to the conversion of methanol to light olefins.

BACKGROUND

The light olefins serve as feed materials for the production of numerous chemicals. Light olefins have traditionally been produced through the processes of steam or catalytic cracking. The limited availability and high cost of petroleum sources, however, has resulted in a significant increase in the cost of producing light olefins from such petroleum sources.

The search for alternative materials for light olefin production has led to the use of oxygenates such as alcohols and, more particularly, to the use of methanol, ethanol, and higher alcohols or their derivatives. The oxygenates are often produced from more plentiful sources of raw materials, such as conversion of natural gas to alcohols, or the production of oxygenates from coal. Molecular sieves such as microporous crystalline zeolite and non-zeolitic catalysts, particularly silicoaluminophosphates (SAPO), are known to promote the conversion of oxygenates to hydrocarbon mixtures, particularly hydrocarbon mixtures composed largely of light olefins.

The amounts of light olefins resulting from such processing can be further increased by reacting, i.e., cracking, heavier hydrocarbon products, particularly heavier olefins such as $C_4$ and $C_5$ olefins, to light olefins. For example, commonly assigned, U.S. Pat. No. 5,914,433 to Marker, the entire disclosure of which is incorporated herein by reference, discloses a process for the production of light olefins comprising olefins having from 2 to 4 carbon atoms per molecule from an oxygenate feedstock. The process comprises passing the oxygenate feedstock to an oxygenate conversion zone containing a metal aluminophosphate catalyst to produce a light olefin stream. A propylene and/or mixed butylene stream is fractionated from said light olefin stream and cracked to enhance the yield of ethylene ($C_2H_4$) and propylene ($C_3H_6$) products. This combination of light olefin product and propylene and butylene cracking in a riser cracking zone or a separate cracking zone provides flexibility to the process which overcomes the equilibrium limitations of the aluminophosphate catalyst. In addition, the invention provides the advantage of extended catalyst life and greater catalyst stability in the oxygenate conversion zone.

With the continued demand for light olefins, there is still a demand for further improvements that will result in increased yields, or reductions in processing costs, or equipment costs.

SUMMARY

The present invention provides a process for utilizing a catalyst at unexpected operating conditions to increase propylene production A first embodiment of the invention is a process for the conversion of oxygenates to light olefins, comprising contacting an oxygenate stream with a catalyst in a fluidized bed at reaction conditions in a reactor to generate a process stream comprising propylene and butylenes, wherein the catalyst comprises SAPO-18, and wherein the reaction conditions include a pressure greater than 2 MPa absolute. An embodiment of the invention is one, any or all of prior embodiments in this paragraph up through the first embodiment in this paragraph wherein the pressure is between 2 MPa and 3.8 MPA. An embodiment of the invention is one, any or all of prior embodiments in this paragraph up through the first embodiment in this paragraph wherein the oxygenates comprise alcohols and ethers. An embodiment of the invention is one, any or all of prior embodiments in this paragraph up through the first embodiment in this paragraph wherein the oxygenates comprise methanol. An embodiment of the invention is one, any or all of prior embodiments in this paragraph up through the first embodiment in this paragraph further comprising passing the process stream to a light olefins recovery unit, thereby generating an ethylene product stream, a propylene product stream and a C4+ product stream; and passing the C4+ product stream to an olefin cracking unit to generate an olefin cracking process stream comprising ethylene and propylene. An embodiment of the invention is one, any or all of prior embodiments in this paragraph up through the first embodiment in this paragraph further comprising passing the olefin cracking process stream to the light olefins recovery unit. An embodiment of the invention is one, any or all of prior embodiments in this paragraph up through the first embodiment in this paragraph wherein the reaction conditions include a temperature of at least 375 C. An embodiment of the invention is one, any or all of prior embodiments in this paragraph up through the first embodiment in this paragraph further comprising passing the process stream to a light olefins recovery unit, thereby generating an ethylene product stream, a propylene product stream and a C4+ product stream; and passing the C4+ product stream and a portion of the ethylene product stream to a metathesis reactor, thereby generating a metathesis stream comprising propylene. An embodiment of the invention is one, any or all of prior embodiments in this paragraph up through the first embodiment in this paragraph further comprising passing the olefin cracking process stream to the light olefins recovery unit. An embodiment of the invention is one, any or all of prior embodiments in this paragraph up through the first embodiment in this paragraph further comprising passing the process stream to a light olefins recovery unit, thereby generating an ethylene product stream, a propylene product stream, a butene product stream and a C5+ product stream; and passing the butene product stream to an oxydehydrogenation butadiene production unit to generate a 1,3 butadiene product stream.

A second embodiment of the invention is a process for the conversion of oxygenates to light olefins, comprising contacting an oxygenate stream with a catalyst in a fluidized bed at reaction conditions in a reactor to generate a process stream comprising olefins, wherein the catalyst comprises SAPO-18, and wherein the reaction conditions include a pressure greater than 2 MPa (absolute); passing the process stream to a light olefins recovery unit, thereby generating an ethylene product stream, a propylene product stream, a C4 product stream, and a C5+ product stream; and passing a portion of the C5+ product stream to an olefins cracking unit to generate an olefins cracking effluent stream comprising propylene. An embodiment of the invention is one, any or all of prior embodiments in this paragraph up through the second embodiment in this paragraph further comprising passing the olefins cracking effluent stream to the light olefins recovery unit. An embodiment of the invention is one, any or all of prior embodiments in this paragraph up through the second embodiment in this paragraph further comprising passing the C4 product stream to a C4 separation unit to generate an isobutene stream and normal butene stream. An embodiment of the invention is one, any or all of prior embodiments in this paragraph up through the second embodiment in this paragraph further comprising passing the C4 product stream to an on-purpose butadiene production unit to generate a butadiene product stream. An embodiment of the invention is one, any or all of prior embodiments in this paragraph up through the second embodiment in this paragraph wherein the oxygenate is methanol. An embodiment of the invention is one, any or all of prior embodiments in this paragraph up through the second embodiment in this paragraph wherein the partial pressure of methanol in the reactor is at least 275 kPa at the inlet.

A third embodiment of the invention is a process for the conversion of methanol to light olefins, comprising contacting a methanol stream with a catalyst in a fluidized bed at reaction conditions in a reactor to generate a process stream comprising olefins, wherein the catalyst comprises SAPO-18, and wherein the reaction conditions include a reactor pressure of at least 2 MPa; and passing the process stream to a light olefins recovery unit, thereby generating an ethylene product stream, a propylene product stream, and a C4+ product stream. An embodiment of the invention is one, any or all of prior embodiments in this paragraph up through the third embodiment in this paragraph further comprising passing the C4+ product stream to an olefin cracking unit to generate an olefin cracking process stream comprising light olefins. An embodiment of the invention is one, any or all of prior embodiments in this paragraph up through the third embodiment in this paragraph further comprising passing the C4+ product stream, and a portion of the ethylene product stream to a metathesis reactor to generate a metathesis process stream comprising propylene. An embodiment of the invention is one, any or all of prior embodiments in this paragraph up through the third embodiment in this paragraph wherein the reaction conditions further include a total pressure in the reactor of between 2 MPa and 4 MPa.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

Other objects, advantages and applications of the present invention will become apparent to those skilled in the art from the following detailed description and drawings.

DETAILED DESCRIPTION

The production of light olefins, ethylene and propylene, are important precursors for products today, Most notably, the principal products are polyethylene and polypropylene. The source of these precursors has been mainly from the cracking of naphtha. Increasingly, other sources for the production of light olefins is sought due to cost considerations and availability of raw materials. Oxygenate, notably methanol, can be converted and is increasingly being used. Methanol can be generated from several sources, including natural gas and coal.

The methanol to olefin (MTO) process has been successfully commercialized. U.S. Pat. No. 6,303,839 presents an integrated MTO-olefin cracking process. The oxygenate feedstock is catalytically converted over a silicoaluminophosphate (SAPO) catalyst. The increase in light olefin production is also described in U.S. Pat. No. 7,317,133 wherein the production of heavier olefins are directed to an olefin cracking reactor to generate a process stream comprising light olefins. The olefin cracking process utilizes a different catalyst from a family of crystalline silicate having an WI or MEL. Examples of these catalysts include ZSM-5 or ZSM-11.

Additional process developments continue to be generated, such as U.S. Pat. No. 7,568,016 that integrates the MTO with an ethylene dimerization process and metathesis process for increasing the propylene yields. The dimerization process can also be used to increase the heavier olefins for other purposes. U.S. Pat. No. 7,732,650 describes a process for the separation of butenes, along with isomerization and metathesis reactions.

Processes are also developed that operate around control conditions of the reactor, such as U.S. Pat. No. 6,137,022, wherein the reaction zone is operated to contain a restricted amount of catalyst, containing 15 volume percent or less, and operation is controlled to limit conversion of the feedstock to between 80 and 99%.

Other aspects include controlling the process with modifications of the catalyst, such as limiting the Si/Al2 ratio to between 0.10 and 0.32 as in U.S. Pat. No. 7,763,765.

While there are many similar patents that cover integrated MTO-OCP process to maximize ethylene and propylene, none of these processes has flexibility to control the Propylene to Ethylene (P/E) product ratio. The P/E product ratio is largely determined by the MTO and OCP reactor yields. A high P/E ratio, preferably more than 3 is desirable due to the increased demand for propylene. Due to this increase in demand for higher propylene over ethylene, it has been discovered that changing the catalyst preference and increasing the pressure substantially has changed not only the product ratios in the MTO process, but the catalyst deactivation rate has been found to decrease, thereby enabling longer cycle times and improved economics.

Figure 1:
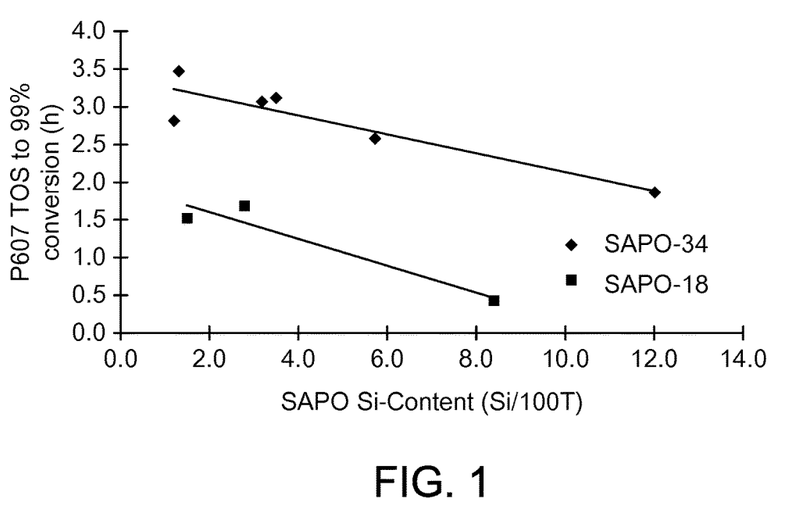
FIG. 1 shows the selectivity of SAPO-34 and SAPO-18 at standard operating pressures.

Different SAPO materials have been tried, and many have been found to work for the conversion of oxygenates to olefins. However, most are very poor and provide low conversion. The principal SAPO for conversion of oxygenates to olefins is SAPO-34, and has an activity that provide for a substantial increase in the time on stream relative to SAPO-18, as seen in FIG. 1. In addition, it can be seen that with increasing silicon content, the time on stream decreases. With the conversion process, it has been found that the conversion occurs best at low pressures. This is due to a combination of factors when setting the operating conditions. When the oxygenate to olefins conversion is operated at high pressures, the catalyst is much more rapidly deactivate due to coking. This deactivation reduces the time in a reactor for the catalyst, increases that amount of time the catalyst is cycled through a regeneration unit, and decreases the life of the catalyst, thereby reducing any economic benefit.

The current method of converting methanol to olefins (MTO) is a process that is designed to maximize the production of ethylene and propylene. The process utilizes a SAPO-34 catalyst and is operated at a relatively low pressure, about 137 kPa partial pressure of methanol. The relatively low pressure is to ensure a good conversion, while limiting the amount of coking on the catalyst during the conversion process. It has also been found to be preferred over SAPO-18 at this pressure as can be seen in FIG. 1. In addition, the catalyst for use in the conversion of methanol to olefins was found to be better when the Si content was relatively low. In terms of the SAPO-35, the content was less than 4%. The Si content is the percent of the Si atoms of the silicon, aluminum and phosphorus atoms that form the molecular sieve framework. The operation of a methanol to olefins conversion reactor is operated at a low pressure to reduce the coking. It has been found that raising the pressure increases coking on the catalyst and accelerates the deactivation of the catalyst. At these pressures, the preferred catalyst is a SAPO-34 catalyst for the best yields and selectivities. This can be readily seen by the performance of the two catalysts showing the light olefin concentrations at breakthrough for the catalysts having varied silica content.

Figure 2A:
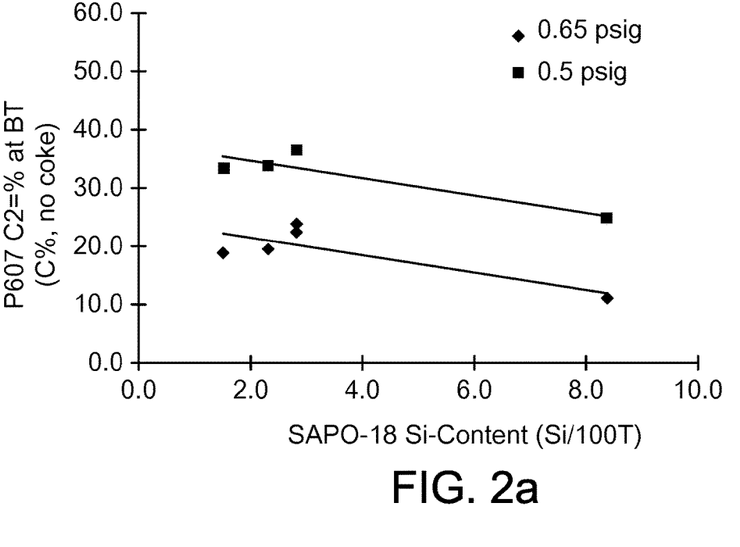
FIGS. 2a and 2b show the ethylene production for SAPO-18 at low pressure and high pressure.
Figure 2B:
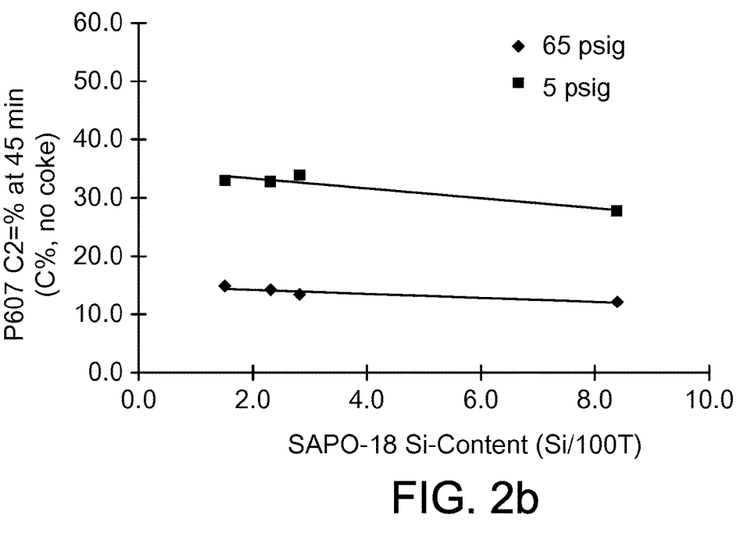
Figure 3A:
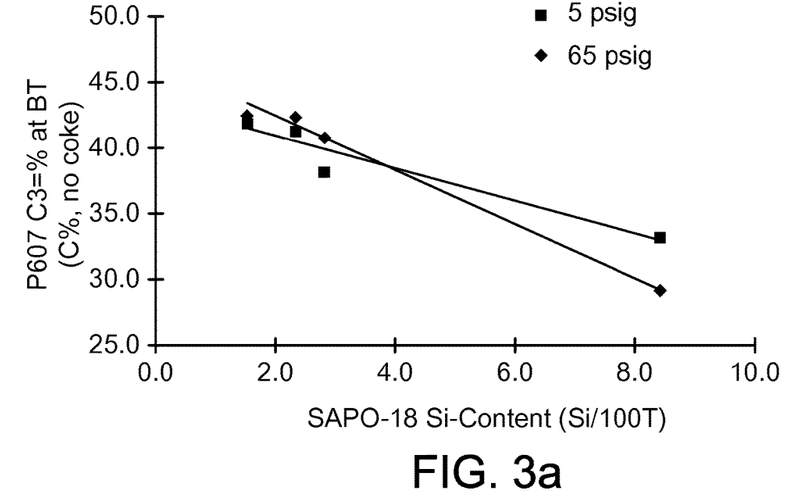
FIGS. 3a and 3b show the propylene production for SAPO-18 at low pressure and high pressure.
Figure 3B:
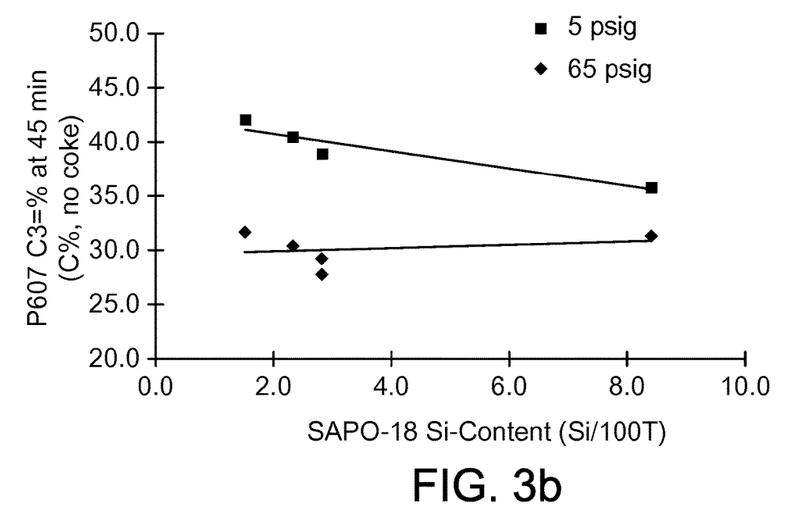
Figure 4A:
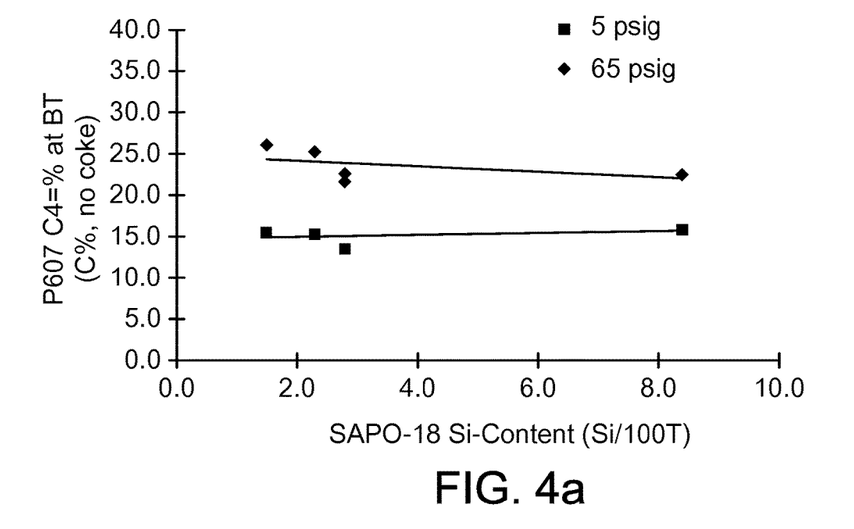
FIGS. 4a and 4b show the butylene production for SAPO-18 at low pressure and high pressure.
Figure 4B:
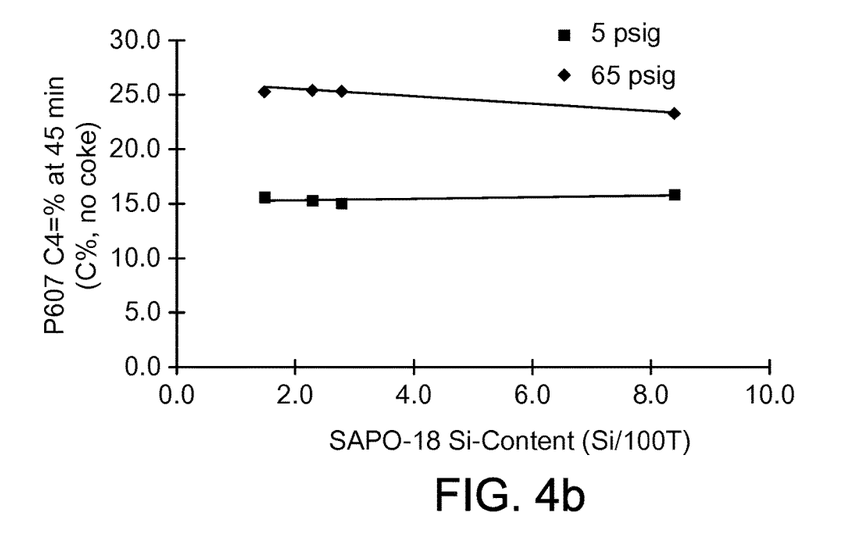

SAPO-34 was found to be superior than SAPO-18 for the production of ethylene and propylene. It was also found that when using SAPO-18, the selectivity for ethylene and propylene fell with increasing pressure, as can be seen in FIGS. 2a and b, and 3a and b. This was true at 45 min. and at breakthrough. However, it was found that SAPO-18 had a greater selectivity for heavier olefins than SAPO-34, and unexpectedly, instead of decreasing selectivity, the selectivity for butylenes increased with increasing pressure, as seen in FIGS. 4a and b.

It has been discovered in testing of SAPO-18, that while SAPO-34 provides for better performance in the production of light olefins over SAPO-18, when a shift in product is desired, that increasing the pressure and utilizing SAPO-18, there in an improvement in the production of propylene and C4+ olefins. The C4+ olefins provide for additional light olefins yields through the olefin cracking process, but also provides for an increased production of C4 olefins, as demand for butyl rubbers increases. Another benefit is a decrease in the normalized coke selectivity relative to the same material when tested at a total reactor pressure of 135 kPa (absolute) (5 psig). Another benefit allows for operation of an MTO reactor with the catalyst occupying an increased volume of the reactor. In one embodiment, the catalyst occupies more than 15 volume % of the reactor.

Figure 5:
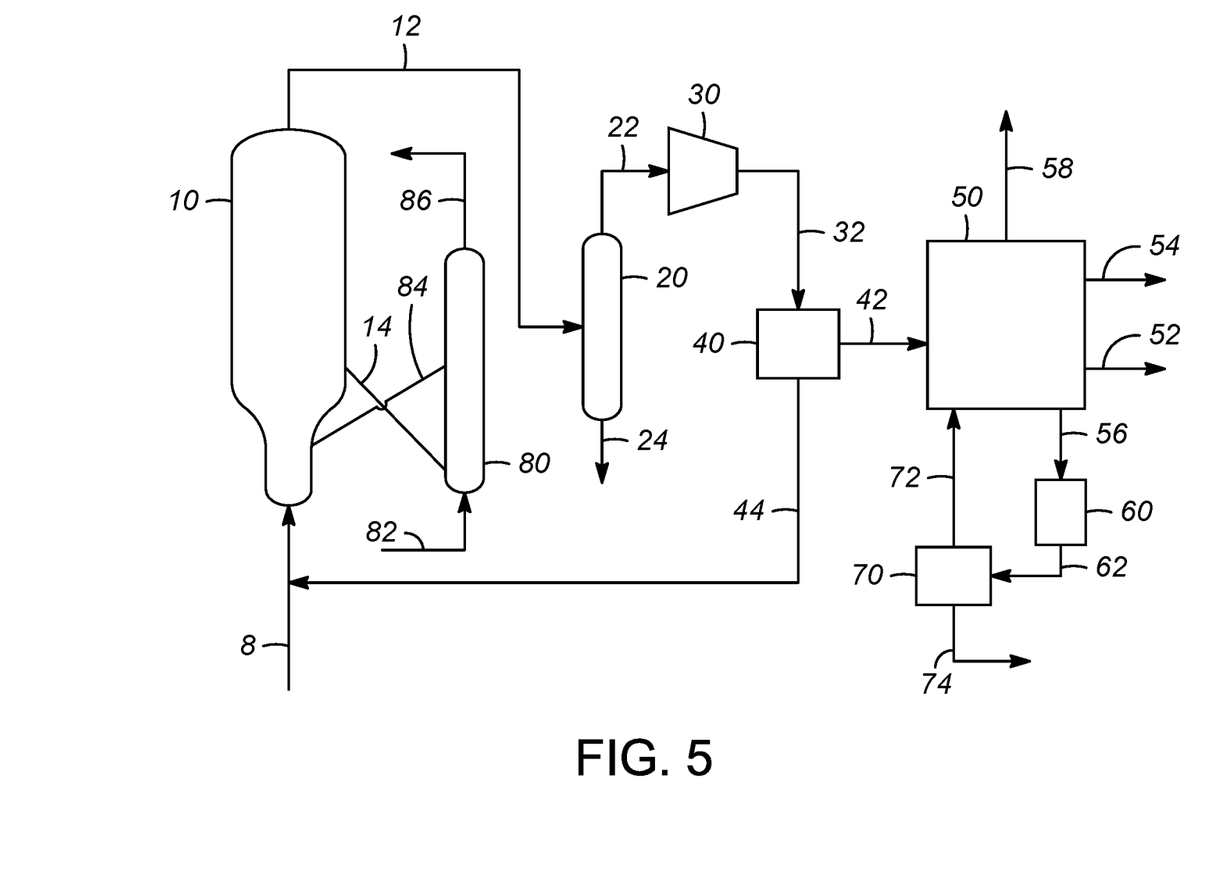
FIG. 5 shows the process flow for the present invention.

The MTO process, as shown in FIG. 5, includes passing a methanol stream 8 to an MTO reactor 10. The MTO reactor 10 generates a process stream 12 comprising light olefins. The process stream 12 is passed to a dewatering column 20 to generate a process stream 22 with reduced water content, and a water stream 24 to pass water for further processing. The process stream 22 is compressed in a compressor 30 to generate a compressed process stream 32. The compressed process stream 32 is passed to a dimethyl ether (DME) recovery unit 40, and generates an olefin rich stream 42 and a DME rich stream 44. The DME rich stream 44 can be recycled to the MTO reactor 10. The olefin rich stream 42 is passed to a light olefin recovery unit 50 where the product streams are generated. Product streams include an ethylene stream 52, a propylene stream 54 and a C4+ stream 56.

The MTO process is enhanced by passing the C4+ stream 56 comprising heavier olefins to a selective hydrogenation process to remove acetylenes and diolefins, and to an olefin cracking process (OCP) 60 to convert heavier olefins to light olefins. The OCP process stream 62 is passed to a separation unit 70 to generate a light olefins stream 72 and a heavy stream 74. The light olefins stream 72 is passed to the light olefins recovery unit 50.

The present invention provides a process for the conversion of oxygenates to light olefins. The process includes contacting an oxygenate stream with a catalyst in a fluidized bed at reaction conditions in an MTO reactor to generate a process stream comprising olefins. The catalyst in the MTO reactor comprises SAPO-18, and the reaction conditions include a pressure greater than 550 kPa (absolute) (65 psig). In one embodiment, the reaction conditions include a pressure between 2 MPa and 4 MPa (absolute).

The process can further include passing the process stream comprising light olefins to a light olefins recovery unit to generate an ethylene stream, a propylene stream and a C4+ product stream. The C4+ product stream, comprising C4+ olefins, is passed to an olefins cracking unit to generate an olefins process stream comprising ethylene and propylene. The olefins process stream is passed to the light olefins recovery unit to recover the additional light olefins.

The preferred oxygenates includes alcohols and ethers, with a preferred oxygenate of methanol.

In one embodiment, the process includes operating at a oxygenate partial pressure of 250 kPa to 300 kPa, with a preferred operating partial pressure of the oxygenate at about 275 kPa (40 psi). This is the partial pressure of the oxygenate at the inlet to the reactor. The oxygenate partial pressure will decrease as the oxygenate is converted to an olefin. A preferred temperature for the reaction conditions includes a temperature greater than 375 C.

In one embodiment, the process includes passing from the MTO reactor to the light olefins recovery unit, thereby generating an ethylene product stream, a propylene product stream and a C4+ product stream. The C4+ product stream and a portion of the ethylene product stream are passed to a metathesis reactor, wherein the metathesis reaction generates a metathesis process stream comprising propylene. The metathesis process stream is passed to the light olefins recovery unit.

The present invention has found that the operation of the less desirable catalyst, SAPO-18, over SAPO-34 produced higher propylene and heavier olefins. The improvement in propylene production reduces the amount of processing of the ethylene through oligomerization or other means to achieve higher propylene yields. In addition the higher heavier content for conversion also is improved. For the metathesis reaction the theoretical stoichiometric ratios of butenes to ethylene (B/E) for conversion to propylene is 2:1. For actual reaction conditions the preferred range for the B/E ratio of the feed to a metathesis reactor is between 2:1 and 2.25:1. At the higher pressures, such as a partial pressure of methanol at 310 kPa, with SAPO-34, the B/E ratio is from 0.2:1 to 0.7:1, which is to low for the efficient conversion. For SAPO-18 at this pressure the B/E ratio was from about 1.5:1 to just above 2:1. Further increasing the partial pressure of the methanol to 1.3 MPa, increase the B/E ratio from 2:1 to over 2.5:1. This shows that SAPO-18 operated at different conditions changes the overall process and allows for flexibility without providing for additional reactors such as oligomerization reactors to boost propylene yields.

One aspect of the present invention is the operation at a higher pressure. This reduces the amount of compression needed for the process stream passed to the light olefins recovery unit. Compression of the process stream can be eliminated by operating the MTO reactor at a sufficiently elevated pressure.

In one embodiment, the present invention is a process for increasing the olefin production in the C2 to C4 range. As C4 olefins become an important product, an increased flexibility for the production of different olefins is important. The process includes passing an oxygenate stream to an oxygenate to olefins reactor, and contacting the oxygenate with the catalyst in a fluidized bed at reaction conditions to generate a process stream comprising olefins. The reaction conditions include using a SAPO-18 catalyst at a pressure greater than 550 kPa (absolute). The process stream 42 comprising olefins is passed to a light olefins recovery unit 50 to generate an ethylene stream 52, a propylene stream 54, a C5+ stream 56, and a butylenes stream 58. The C5+ stream 56 can be passed to a secondary reactor 60 to generate a secondary stream 62 comprising light olefins and butylenes. The secondary stream 62 is passed to a separation unit 70 to generate a light stream 72 comprising C2 to C4 hydrocarbons and a heavy stream comprising C5+ hydrocarbons. The light stream 72 is passed to the light olefins recovery unit 50.

The process can further include passing the butylenes stream 58 to a C4 separation unit to generate an isobutene stream and normal butene stream.

In one embodiment, the secondary reactor 60 is a metathesis reactor. The C5+ stream 56 and a portion of the ethylene stream 52 can be passed to the metathesis reactor to generate a metathesis stream 62 comprising butenes and propylene.

In another embodiment, the secondary reactor 60 is an olefin cracking reactor. The C5+ stream is passed to the olefin cracking reactor to generate an olefins cracking process stream 62 comprising light olefins and butylenes.

This provides an economic advantage for providing increased flexibility to shift from one product to another, as the economic value shifts for the different products. That is, when the value of butylenes increases relative to ethylene or propylene.

The process conditions include, preferably a partial pressure of the oxygenate, methanol at a pressure of at least 275 kPa, with a total pressure of the reactor of at least 550 kPa (absolute).

The oxygenate to olefins reactor conditions are preferred to operate in the vapor phase. Typical reaction conditions desirably occur at a temperature in the range of about 200° C. to about 300° C., with a temperature of about 240° C. to about 260° C., e.g., at about 250° C., being preferred. The pressure will be in the range of about 300 to about 1500 kPa, with a pressure in the range of about 400 to about 700 kPa preferred, and with a pressure of at least 550 kPa being most preferred. A weight hourly space velocity ("WHSV") is in the range of about 2 to about 15 $hr^{-1}$, with a WHSV in the range of about 3 to about 7 $hr^{-1}$, e.g., about 5 $hr^{-1}$, being preferred.

The fluidized bed reactor 10 is part of a system with continuous catalyst regeneration. The catalyst in the reactor 10 is separated from the process stream and passed out a catalyst channel 14, to the regenerator 80. An oxidizing gas stream 82 is passed to the regenerator 80 to burn off the coke deposits and to regenerate the catalyst. A regenerated catalyst stream 84 is passed back to the reactor 10, and a combustion effluent gas 86 is passed out of the regenerator.

While the following is described in conjunction with specific embodiments, it will be understood that this description is intended to illustrate and not limit the scope of the preceding description and the appended claims.

A first embodiment of the invention is a process for the production of light olefins from an oxygenate feed, comprising passing the oxygenate feed to an MTO reactor, wherein the reactor comprises an MTO catalyst comprising a silicoaluminophosphate, and is operated at reaction conditions to generate an effluent stream comprising olefins with a desired distribution of ethylene, propylene, and butylenes. An embodiment of the invention is one, any or all of prior embodiments in this paragraph up through the first embodiment in this paragraph wherein the MTO reactor is a fluidized bed. An embodiment of the invention is one, any or all of prior embodiments in this paragraph up through the first embodiment in this paragraph wherein the silicoaluminophosphate is SAPO-18, SAPO-34, SAPO-5 or combinations thereof. An embodiment of the invention is one, any or all of prior embodiments in this paragraph up through the first embodiment in this paragraph wherein the silicoaluminophosphate is SAPO-18. An embodiment of the invention is one, any or all of prior embodiments in this paragraph up through the first embodiment in this paragraph wherein the oxygenates comprise alcohols, aldehydes and ethers. An embodiment of the invention is one, any or all of prior embodiments in this paragraph up through the first embodiment in this paragraph wherein the oxygenate comprises methanol and dimethyl ether. An embodiment of the invention is one, any or all of prior embodiments in this paragraph up through the first embodiment in this paragraph wherein the oxygenate comprises methanol. An embodiment of the invention is one, any or all of prior embodiments in this paragraph up through the first embodiment in this paragraph wherein the process pressure and temperature are set to provide a desired distribution of ethylene, propylene, and butylenes. An embodiment of the invention is one, any or all of prior embodiments in this paragraph up through the first embodiment in this paragraph wherein the inlet partial pressure of the oxygenate is between 0.1 MPa and 2.5 MPa and preferably between 0.2 MPa and 2.0 MPa. An embodiment of the invention is one, any or all of prior embodiments in this paragraph up through the first embodiment in this paragraph wherein the process temperature is between 300° C. and 500° C. and preferably between 375° C. and 475° C. An embodiment of the invention is one, any or all of prior embodiments in this paragraph up through the first embodiment in this paragraph further comprising passing the effluent stream to a light olefins recovery unit. An embodiment of the invention is one, any or all of prior embodiments in this paragraph up through the first embodiment in this paragraph further comprising passing the effluent stream to a quench tower to generate a water stream and a dewatered effluent stream; passing the dewatered effluent stream to a compressor to generate a compressed stream; passing the compressed stream to a DME recovery unit to generate a DME stream and a DME olefins stream; and passing the DME olefins stream to a light olefins recovery unit to generate an ethylene stream, a propylene stream and a C4+ heavies stream. An embodiment of the invention is one, any or all of prior embodiments in this paragraph up through the first embodiment in this paragraph further comprising passing the heavies stream to an olefin cracking unit to generate an olefins cracking effluent stream comprising light olefins. An embodiment of the invention is one, any or all of prior embodiments in this paragraph up through the first embodiment in this paragraph further comprising passing the olefins cracking effluent stream to the light olefins recovery unit. An embodiment of the invention is one, any or all of prior embodiments in this paragraph up through the first embodiment in this paragraph further comprising passing the effluent stream to a quench tower to generate a water stream and a dewatered effluent stream; passing the dewatered effluent stream to a compressor to generate a compressed stream; passing the compressed stream to a DME recovery unit to generate a DME stream and a DME olefins stream; and passing the DME olefins stream to a light olefins recovery unit to generate an ethylene stream, a propylene stream, a C4 olefin stream and a C5+ heavies stream. An embodiment of the invention is one, any or all of prior embodiments in this paragraph up through the first embodiment in this paragraph further comprising passing a portion or all of the C4 olefin product stream and a portion or all of the ethylene product stream to a metathesis reactor, thereby generating a metathesis stream comprising mostly of propylene. An embodiment of the invention is one, any or all of prior embodiments in this paragraph up through the first embodiment in this paragraph further comprising passing the C5+ heavies stream to an olefin cracking unit to generate an olefins cracking effluent stream comprising light olefins. An embodiment of the invention is one, any or all of prior embodiments in this paragraph up through the first embodiment in this paragraph further comprising passing the olefins cracking effluent stream to the light olefins recovery unit. An embodiment of the invention is one, any or all of prior embodiments in this paragraph up through the first embodiment in this paragraph further comprising passing the effluent stream to a quench tower to generate a water stream and a dewatered effluent stream; passing the dewatered effluent stream to a compressor to generate a compressed stream; passing the compressed stream to a DME recovery unit to generate a DME stream and a DME olefins stream; and passing the DME olefins stream to a light olefins recovery unit to generate an ethylene stream, a propylene stream, a C4 olefin stream, a C5 olefin stream and a C6+ heavies stream. An embodiment of the invention is one, any or all of prior embodiments in this paragraph up through the first embodiment in this paragraph further comprising passing a portion or all of the C5 product stream and a portion or all of the ethylene product stream to a metathesis reactor, thereby generating a metathesis stream comprising mostly propylene and butenes. An embodiment of the invention is one, any or all of prior embodiments in this paragraph up through the first embodiment in this paragraph further comprising passing the C4 product stream to a C4 separation unit to generate an isobutene stream and normal butene stream. An embodiment of the invention is one, any or all of prior embodiments in this paragraph up through the first embodiment in this paragraph further comprising passing the normal butene stream to an oxidative dehydrogenation reactor, thereby generating an on purpose butadiene stream consisting of butadiene. An embodiment of the invention is one, any or all of prior embodiments in this paragraph up through the first embodiment in this paragraph further comprising passing the C6+ heavies stream to an olefin cracking unit to generate an olefins cracking effluent stream comprising light olefins. An embodiment of the invention is one, any or all of prior embodiments in this paragraph up through the first embodiment in this paragraph further comprising passing the olefins cracking effluent stream to the light olefins recovery unit. An embodiment of the invention is one, any or all of prior embodiments in this paragraph up through the first embodiment in this paragraph further comprising passing the effluent stream to a quench tower to generate a water stream and a dewatered effluent stream; passing the dewatered effluent stream to a compressor to generate a compressed stream; passing the compressed stream to a DME recovery unit to generate a DME stream and a DME olefins stream; and passing the DME olefins stream to a light olefins recovery unit to generate an ethylene stream, a propylene stream, a C4 olefin stream, a C5 product stream and a C6+ heavies stream. An embodiment of the invention is one, any or all of prior embodiments in this paragraph up through the first embodiment in this paragraph further comprising passing the C5 heavy stream and the ethylene product stream to a metathesis reactor, thereby generating a metathesis stream comprising propylene and butenes. An embodiment of the invention is one, any or all of prior embodiments in this paragraph up through the first embodiment in this paragraph further comprising passing the C4 product stream to a C4 separation unit to generate an isobutene stream and normal butene stream. An embodiment of the invention is one, any or all of prior embodiments in this paragraph up through the first embodiment in this paragraph further comprising passing the C6+ heavies stream to an olefin cracking unit to generate an olefins cracking effluent stream comprising light olefins. An embodiment of the invention is one, any or all of prior embodiments in this paragraph up through the first embodiment in this paragraph further comprising passing the olefins cracking effluent stream to the light olefins recovery unit.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for the production of light olefins from an oxygenate feed comprising at least one of an alcohol, an aldehyde and/or an ether, the process comprising passing the oxygenate feed to a single OTO reactor, wherein the reactor comprises a catalyst comprising SAPO-18 having a Si content of less than 4-wt. % wherein the catalyst occupies greater than 15 volume % of the reactor and wherein the reactor is operated at reaction conditions including a partial pressure of the oxygenate of from greater than 310 kPa to 1.3 MPa, a temperature of from about 375° C. to about 475° C., and a WHSV of from about 3 to about 7 hr$^{-1}$ to generate an effluent stream comprising ethylene, propylene, and butenes, with a butenes to ethylene weight ratio of about 2:1 or greater;

passing the effluent stream to a quench tower to generate a water stream and a dewatered effluent stream;

passing the dewatered effluent stream to a compressor to generate a compressed stream;

passing the compressed stream to a DME recovery unit to generate a DME stream and a DME olefins stream;

passing the DME olefins stream to a light olefins recovery unit to generate an ethylene stream, a propylene stream, a C4 olefin stream, a C5 olefin stream and a C6+ heavies stream; and passing a portion or all of the C5 olefin stream and a portion or all of the ethylene stream to a metathesis reactor, thereby generating a metathesis stream comprising mostly propylene and butenes.

2. The process of claim 1 wherein the MTO reactor is a fluidized bed.

3. The process of claim 1 wherein the oxygenate feed comprises methanol and dimethyl ether.

4. The process of claim 1 wherein the oxygenate feed comprises methanol.

5. The process of claim 1 wherein a process pressure and temperature are set to provide a desired distribution of ethylene, propylene, and butenes.

6. The process of claim 1 further comprising passing the C4 olefin stream to a C4 separation unit to generate an isobutene stream and normal butene stream.

7. The process of claim 6 further comprising passing the normal butene stream to an oxidative dehydrogenation reactor, thereby generating an on purpose butadiene stream consisting of butadiene.

8. The process of claim 1 further comprising passing the C6+ heavies stream to an olefin cracking unit to generate an olefins cracking effluent stream comprising light olefins.

9. The process of claim 8 further comprising passing the olefins cracking effluent stream to the light olefins recovery unit.

* * * * *